(12) United States Patent
Chen et al.

(10) Patent No.: US 11,172,806 B2
(45) Date of Patent: Nov. 16, 2021

(54) MEDICAL MICRO-CABLE STRUCTURE AND CONNECTION METHOD WITH MINI CAMERA CUBE CHIP

(71) Applicant: OmniVision Technologies, Inc., Santa Clara, CA (US)

(72) Inventors: Teng-Sheng Chen, Hsinchu (TW); Wei-Feng Lin, Hsinchu (TW); Xiang-Dong Xiong, Milpitas, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 16/796,087

(22) Filed: Feb. 20, 2020

(65) Prior Publication Data

US 2021/0259528 A1  Aug. 26, 2021

(51) Int. Cl.
*A61B 1/00* (2006.01)
*H04N 5/225* (2006.01)
*H04N 5/232* (2006.01)
*A61B 1/04* (2006.01)

(52) U.S. Cl.
CPC ...... *A61B 1/00124* (2013.01); *A61B 1/00009* (2013.01); *A61B 1/00045* (2013.01); *A61B 1/00114* (2013.01); *A61B 1/04* (2013.01); *H04N 5/2251* (2013.01); *H04N 5/23229* (2013.01); *H04N 2005/2255* (2013.01)

(58) Field of Classification Search
CPC .......................... A61B 1/00; H04N 2005/2255
USPC .......................................................... 348/75
See application file for complete search history.

(56) References Cited

U.S. PATENT DOCUMENTS

| 5,614,943 A * | 3/1997 | Nakamura | H04N 5/23227 348/72 |
| 8,803,960 B2 | 8/2014 | Sonnenschein et al. | |
| 2012/0161857 A1* | 6/2012 | Sakaguchi | H01L 27/0222 327/536 |
| 2014/0343358 A1* | 11/2014 | Hameed | G02B 23/2423 600/109 |
| 2015/0103140 A1* | 4/2015 | Kostuk | A61B 1/00163 348/40 |
| 2019/0099163 A1* | 4/2019 | Morimoto | A61B 8/546 |
| 2020/0359877 A1* | 11/2020 | Seow | A61B 1/00149 |

* cited by examiner

*Primary Examiner* — Amir Shahnami
(74) *Attorney, Agent, or Firm* — Larry E. Henneman, Jr.; Henneman & Associates, PLC (57) ABSTRACT

A novel endoscope includes a camera module, an electrical cable, and an electrical connector. The camera module includes an analog image signal output terminal. The cable includes an analog image signal line having a first end connected to the analog image signal output terminal of the camera module. The electrical connector includes a set of electrical contacts configured to engage a complimentary set of electrical contacts of a host system. The set of electrical contacts includes at least an analog image signal contact connected to a second end of the analog image signal line of the cable.

30 Claims, 9 Drawing Sheets

MEDICAL MICRO-CABLE STRUCTURE AND CONNECTION METHOD WITH MINI CAMERA CUBE CHIP

BACKGROUND OF THE INVENTION

Field of the Invention

This invention relates generally to medical devices, and more particularly to endoscopes.

Description of the Background Art

Endoscopes have become commonplace in the medical industry. Such devices typically include a small digital camera attached to the end of a cable and/or tube. During an endoscopic procedure, the camera is inserted into a patient's body through either a natural orifice or an incision. Because of the invasive nature of such procedures, it is essential that endoscopes are designed to be as small as possible. One challenge in minimizing the size of an endoscope is that image and video quality are sacrificed. Of course, in manufacturing such endoscopes, it is important to minimize manufacturing costs.

What is needed, therefore, is a smaller and less expensive endoscope capable of capturing high quality images and videos.

SUMMARY

The present invention overcomes the problems associated with the prior art by providing a smaller, less expensive endoscope that is capable of capturing high quality images and videos. The invention makes it more practical to dispose of the endoscope after a single use, thereby eliminating the cost and labor of cleaning and sterilization between procedures, and also eliminates the chance of cross-contamination between patients.

An example endoscope includes a camera module, a flexible, electrical cable, and an electrical connector. The camera module includes a clock signal input terminal, an analog image signal output terminal, a power terminal, and a reference terminal. The flexible, electrical cable includes a clock signal line, an analog image signal line, a power line and a reference line. The clock signal line has a first end coupled to the clock signal input terminal of the camera module, and the analog image signal line has a first end electrically coupled to the analog image signal output terminal of the camera module. The power line has a first end electrically coupled to the power terminal of the camera module, and the reference line has a first end electrically coupled to the reference terminal of the camera module. The electrical connector includes a set of electrical contacts configured to engage a complimentary set of electrical contacts of a host system. The set of electrical contacts includes a clock contact electrically couple to a second end of the clock signal line, an analog image signal contact electrically coupled to a second end of the analog image signal line, a power contact electrically coupled to a second end of the power line, and a reference contact electrically coupled to a second end of the reference line.

The example endoscope can be used in conjunction with a display system. An example display system includes a complementary electrical connector, an image signal processor, and a display. The complementary electrical connector is configured to engage the electrical connector of the endoscope. The image signal processor is connected to receive an analog image signal via the complementary connector and is operative to process the analog image signal to produce digital image output. The display is coupled to receive the digital image output from the image signal processor and is operative to display images corresponding to the digital image output.

The flexible electrical cable can further include an electrically insulating jacket, coaxially disposed around the clock signal line, and a conductive shield, coaxially disposed around the electrically insulating jacket. The conductive shield is electrically insulated from the clock signal line and is in electrical contact with the reference line. In a particular example embodiment, the clock signal line, the electrically insulating jacket, and the conductive shield are integral parts of a coaxial cable.

In an example endoscope, the flexible electrical cable further includes a first electrically insulating jacket and a first conductive shield. The first electrically insulating jacket is coaxially disposed around the analog image signal line, and a first conductive shield is coaxially disposed around the first electrically insulating jacket. The first conductive shield is electrically insulated from the analog image signal line and is in electrical contact with the reference line. The flexible electrical cable further includes a second electrically insulating jacket and a second insulating jacket. The second electrically insulating jacket is coaxially disposed around the clock signal line, and the second conductive shield is coaxially disposed around the second electrically insulating jacket. The second conductive shield is electrically insulated from the clock signal line and the second conductive shield is in electrical contact with the first conductive shield and the reference line. The flexible electrical cable further includes a third conductive shield and a non-conductive sheath. The third conductive shield is disposed around and in electrical contact with the first conductive shield, the second conductive shield, and the reference line, and the non-conductive sheath is coaxially disposed around the third conductive shield. The flexible electrical cable further includes a third electrically insulating jacket and a fourth conductive shield. The third electrically insulating jacket is coaxially disposed around the power line, and the fourth conductive shield is coaxially disposed around the third electrically insulating jacket. The fourth conductive shield is electrically insulated from the power line and is in electrical contact with the first conductive shield, the second conductive shield, the third conductive shield, and the reference line. The third conductive shield is also disposed around the fourth conductive shield.

In an example endoscope, the analog image signal line, the first electrically insulating jacket, and the first conductive shield can be integral parts of a coaxial cable. In addition, the reference line can be a ground line.

In an example endoscope, the electrical connector can include a printed circuit board. The clock contact, the analog image signal contact, the power contact, and/or the reference contact can be formed on the printed circuit board. The connector can be adhered, sealed, or otherwise fastened to the cable.

In an example endoscope, the camera module is sealed to the cable. Optionally, the example endoscope further includes an intermediate mount. The intermediate mount includes a first side and a second side opposite the first side. The first side has a first contact, a second contact, a third contact, and a fourth contact. The first contact is electrically connected to the first end of the clock signal line, and the second contact is electrically connected to the first end of the analog image signal line. The third contact is electrically connected to the first end of the power signal line, and the fourth contact is electrically connected to the first end of the reference line.

The second side also has a first contact, a second contact, a third contact, and a fourth contact. The first contact of the second side is electrically connected to the clock signal input terminal of the camera module, and the second contact of the second side is electrically connected to the analog image signal output terminal of the camera module. The third contact of the second side is electrically connected to the power terminal of the camera module, and the fourth contact of the second side is electrically connected to the reference terminal of the camera module.

In addition, the contacts of the first side of the intermediate mount are electrically coupled to the contacts of the second side of the intermediate mount in corresponding fashion. In particular, the first contact of the first side of the intermediate mount is electrically coupled to the first contact of the second side of the intermediate mount, and the second contact of the first side of the intermediate mount is electrically coupled to the second contact of the second side of the intermediate mount. In addition, the third contact of the first side of the intermediate mount is electrically coupled to the third contact of the second side of the intermediate mount, and the fourth contact of the first side of the intermediate mount is electrically coupled to the fourth contact of the second side of the intermediate mount.

In an alternative example endoscope, the first end of the clock signal line is electrically connected directly to the clock signal input terminal of the camera module, and the first end of the analog image signal line is electrically connected directly to the analog image signal output terminal of the camera module. Similarly, the first end of the power line is electrically connected directly to the power terminal of the camera module, and the first end of the reference line is electrically connected directly to the reference terminal of the camera module.

Optionally, the diameter of the power line can be greater than the diameter of the analog image signal line. In addition, the diameter of the power line can be greater than the diameter of the clock signal line.

Any of the example endoscopes can include a conductive shield disposed around the clock signal line, the analog image signal line, the power line, and the reference line, in combination with a non-conductive sheath disposed around the conductive shield.

Methods of manufacturing endoscopes are also disclosed. On example method of manufacturing an endoscope includes providing a camera module including a clock signal input terminal, an analog image signal output terminal, a power terminal, and a reference terminal. The method additionally includes providing a flexible, electrical cable including a clock signal line having a first end and a second end, an analog image signal line having a first end and a second end, a power line having a first end and a second end, and a reference line having a first end and a second end. The method further includes electrically coupling the first end of the clock signal line of the cable to the clock signal input terminal of the camera module, electrically coupling the first end of the analog image signal line of the cable to the analog image signal output terminal of the camera module, electrically coupling the first end of the power line of the cable to the power terminal of the camera module, and electrically coupling the first end of the reference line of the cable to the reference terminal of the camera module. The method continues with providing an electrical connector including a set of electrical contacts configured to engage a complimentary set of electrical contacts of a host system. The set of electrical contacts includes a clock contact, an analog image signal contact, a power contact, and a reference contact. The method additionally includes electrically coupling the clock contact of the electrical connector to the second end of the clock signal line of the cable, electrically coupling the analog image signal contact of the electrical connector to the second end of the analog image signal line of the cable, electrically coupling the power contact of the electrical connector to the second end of the power line of the cable, and electrically coupling the reference contact of the electrical connector to the second end of the reference line of the cable.

Optionally, the example method further includes providing a non-conductive material and encapsulating one or more of the contacts in the non-conductive material. For example, the clock contact of the electrical connector and the second end of the clock signal line of the cable can be encapsulated in the non-conductive material. Similarly, the first end of the analog image signal line of the cable and the analog image signal output terminal of the camera module can be encapsulated in the non-conductive material, and the first end of the power line of the cable and the power terminal of the camera module can encapsulated in the non-conductive material. Furthermore, the first end of the reference line of the cable and the reference terminal of the camera module can be encapsulated in the non-conductive material.

BRIEF DESCRIPTION OF THE DRAWINGS

The present invention is described with reference to the following drawings, wherein like reference numbers denote substantially similar elements.

DETAILED DESCRIPTION

The present invention overcomes the problems associated with the prior art, by providing a more compact endoscope. In the following description, numerous specific details are set forth (e.g., line impedances, wire materials, etc.) in order to provide a thorough understanding of the invention. Those skilled in the art will recognize, however, that the invention may be practiced apart from these specific details. In other instances, details of well-known electrical cable manufacturing practices (e.g., coaxial cable formation, etc.) and components have been omitted, so as not to unnecessarily obscure the present invention.

The term "image data", as used herein, includes, without limitation, data indicative of still images and/or videos. Likewise, the term "image signal" includes, without limitation, signals indicative of still images and/or videos.

Figure 1:
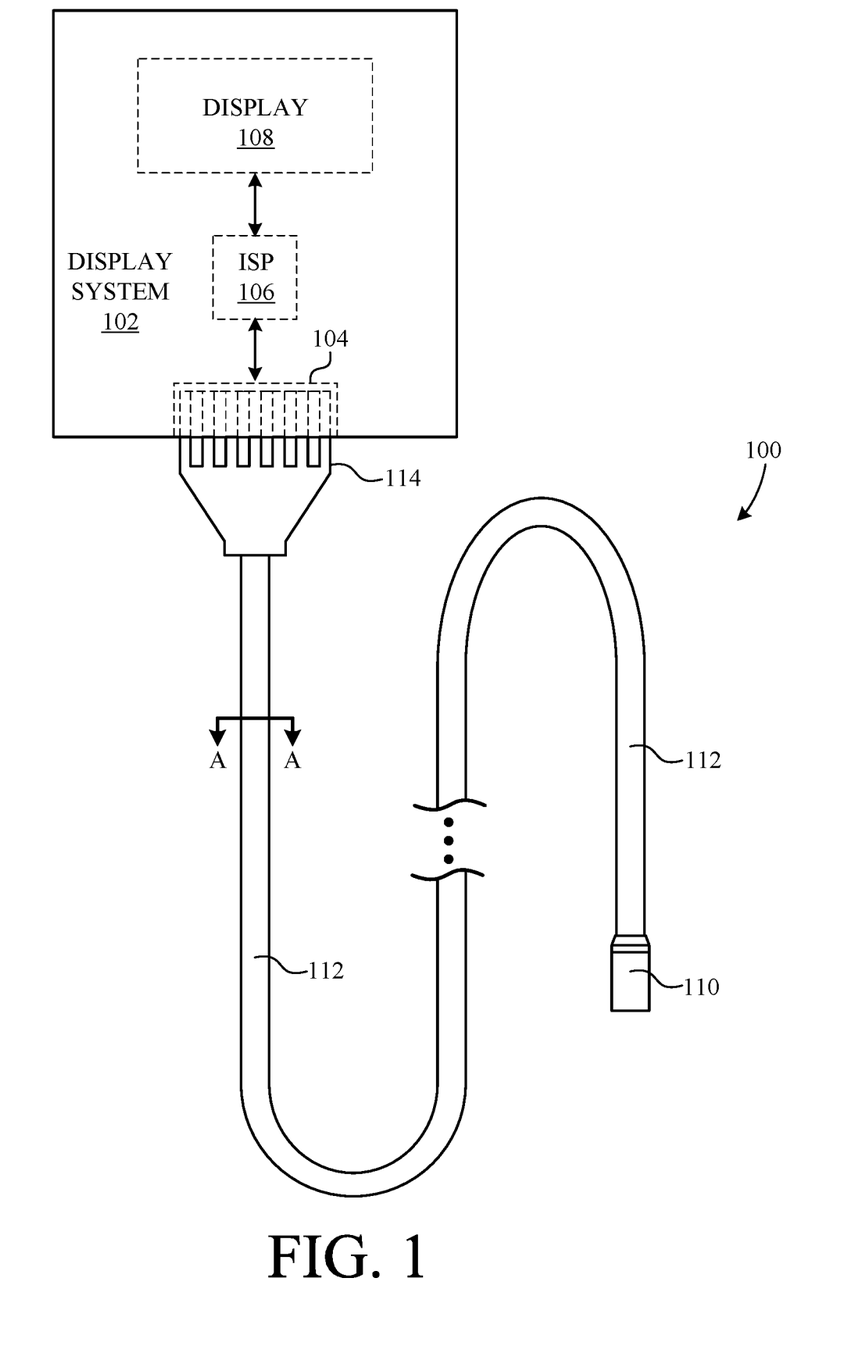
FIG. 1 shows an endoscope connected to a hosting display system according to an example embodiment of the present invention.

FIG. 1 shows an endoscope 100 connected to a hosting display system 102. In this example, endoscope 100 is removably plugged into a socket 104 of hosting device 102. Socket 104 facilitates the physical attachment of endoscope 100 to system 102 and also electrical communication and power transmission therebetween.

During operation, endoscope 100 captures images and/or videos that are then displayed by system 100. More specifically, endoscope 100 captures images and/or videos and outputs the analog image signals indicative of the images to an image signal processor (ISP) 106 of system 102. After receiving the analog image signals, ISP 106 converts them into digital image data that is then output to a display 108 (e.g., a liquid crystal display screen or any other type of display) of system 102. Finally, the digitized image data is displayed by display 108 in the form of images and videos captured by endoscope 100.

In this particular example embodiment, ISP 106 is an OV426 chip manufactured by OmniVision Technologies of Santa Clara, Calif. However, those skilled in the art will recognize that other ISP's having analog-to-digital conversion capabilities can be used in place of the OV426 without departing from the main scope of the present invention.

Endoscope 100 includes a camera module 110, a flexible cable 112, and a connector 114. Camera module 110 is coupled to a first end of cable 112 and connector 114 is coupled to an opposite second end of cable 112. Camera module 110 captures images and transmits the corresponding analog image signals to connector 114 along cable 112. Cable 112 also transfers clock signals and power from system 100 to camera module 110. Indeed, cable 112 includes a plurality of electrical lines (e.g., power line(s), signal line(s), etc.) that are electrically isolated from one another. The respective impedances of the various electrical lines of cable 100 are specifically tailored to minimize noise that could otherwise degrade the quality of the signals transferred along cable 112. Connector 114 is configured to be plugged into socket 104 of system 100 to provide both a physical and electrical connection therebetween.

An advantageous aspect of this example embodiment is that image signals can be output to the host system in the form of analog image signals. This allows the image processing to be carried out by the host system rather than in the endoscope, and eliminates the need for endoscope 100 to include an internal image signal processor. As a result, endoscope 100 is much smaller and less expensive to manufacture than endoscopes having onboard image signal processors. As a result, it is much more practical to treat endoscope 100 as a disposable item, thereby eliminating the need for cleaning and sterilization, and also eliminating the chance of cross-contamination between patients. Another example advantage of not having an onboard image signal processor is that endoscope 100 generates much less heat during operation.

Figure 2:
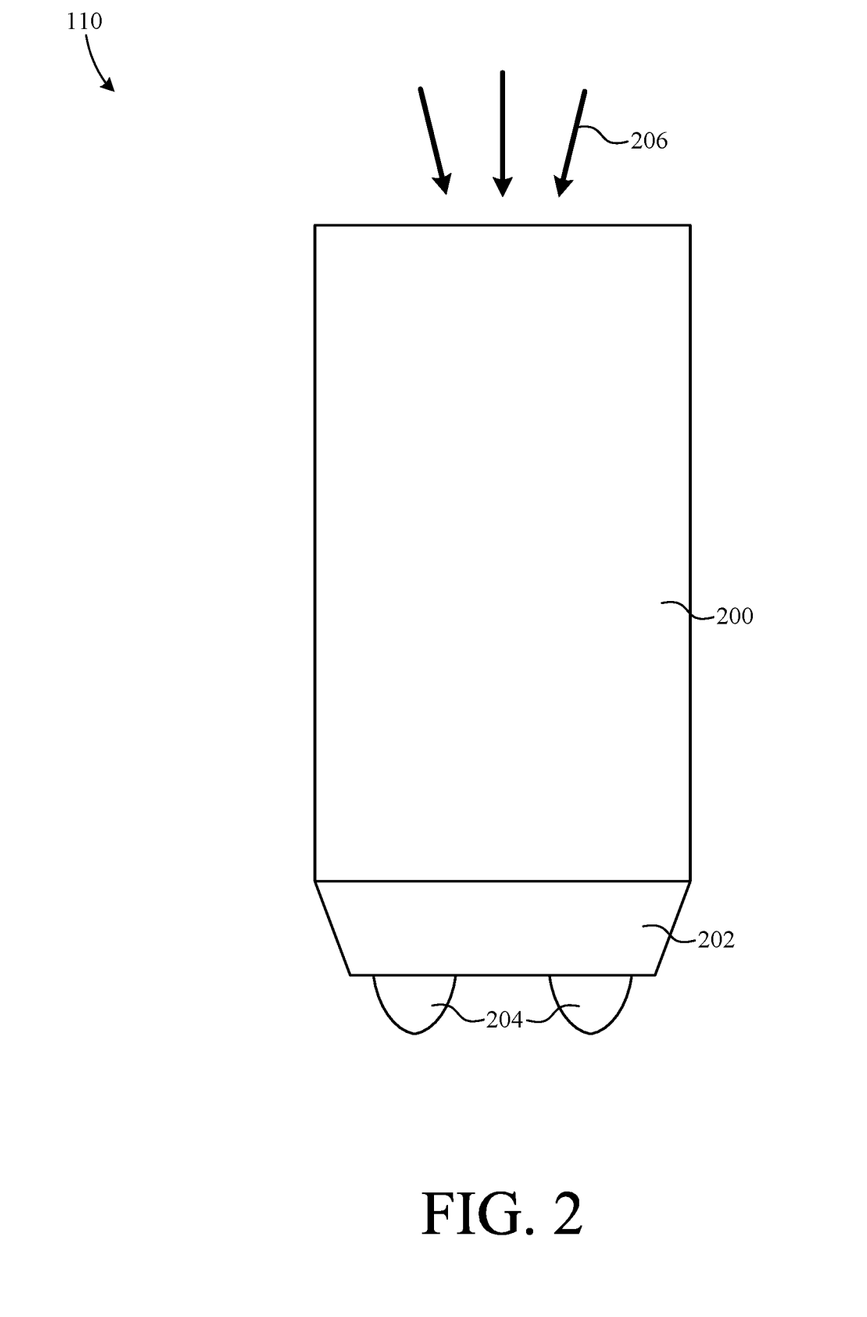
FIG. 2 shows a side view of the camera module of FIG. 1.

FIG. 2 shows a side view of camera module 110 removed from cable 112. Camera module 110 includes an optical assembly 200, an image sensor assembly 202, and a plurality of electrical contacts 204. Optical assembly 200 is attached to a first side of image sensor assembly 202 and electrical contacts 204 are formed on a second opposite side of image sensor assembly 202. Optical assembly 200 includes, for example, a stack of various optical elements (e.g., lenses, filters, etc.) configured to focus light 206 onto image sensor assembly 202. Light 206 impinges upon image sensor assembly 202 and is then converted into electrical signals indicative of an image formed by light 206. The electrical signals are then output from camera module 110 through electrical contacts 204 in the form of analog signals, which may or may not be amplified by image sensor assembly 202 before being output through one of electrical contacts 204. Image sensor assembly 202 includes an image capture chip such as, for example, a CMOS image sensor, a CCD image sensor, etc. Electrical contacts 204 facilitate the electrical connection between image capture assembly 202 and cable 112. In this particular embodiment, electrical contacts 204 are solder bumps formed on image sensor assembly 202 but may alternately include other types of electrical connection means such as, for example, stud bumps, electrical pins, female wire sockets, etc.

In the example embodiment, camera module 110 is an OVM6948 CameraCubeChip™ manufactured by OmniVision Technologies of Santa Clara, Calif. However, those skilled in the art will recognize that other camera modules capable of outputting analog image signals can be used in place of the OVM6948 without departing from scope of the present invention. For example, the OVM6946 CameraCubeChip™ manufactured by OmniVision Technologies (or camera modules from other manufacturers) can be substituted for the OVM6948.

Figure 3:
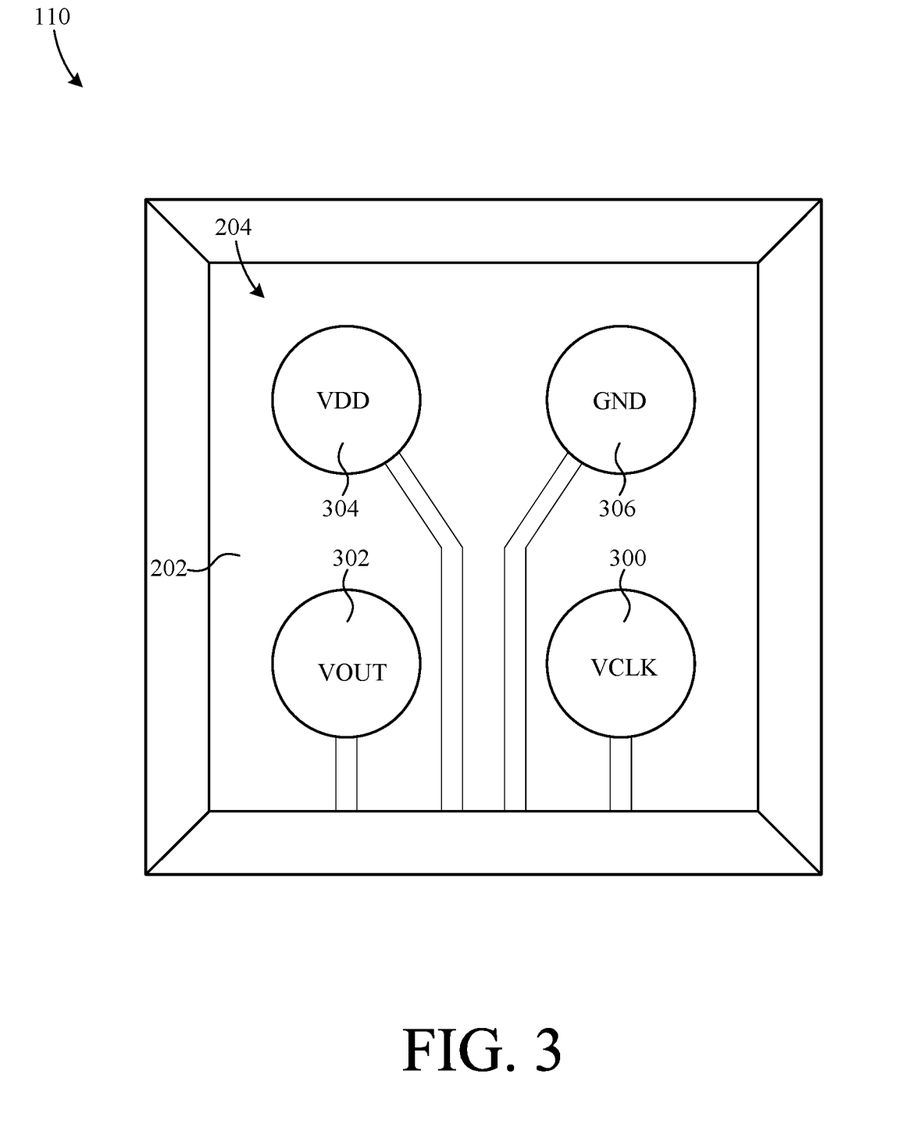
FIG. 3 shows a bottom view of the camera module of FIG. 1.

FIG. 3 shows a bottom view of camera module 110 removed from cable 112. As shown, contacts 204 include a clock signal input terminal 300, an analog image signal output terminal 302, a power terminal 304, and a reference terminal 306. Clock signal input terminal 300 is configured to receive clock signals (e.g. a 4 MHz clock signal) from system 102 through cable 112. The clock signals facilitate the coordination and synchronization of internal functions of the internal circuitry of image capture assembly 202. Analog image signal output terminal 302 outputs analog signals indicative of images captured by the internal image capture chip of image capture assembly 202. Analog image signal output terminal 302 may also function to receive operational instructions output by system 102 to camera module 110 through cable 112. Power terminal 304 receives operating power (e.g. 3.3V) from system 102 that is supplied to camera module 110 through cable 112. Reference terminal 306 is, for example, an electrical ground terminal of camera module 110 that is electrically connected to the electrical ground of system 102 through cable 112.

Figure 4:
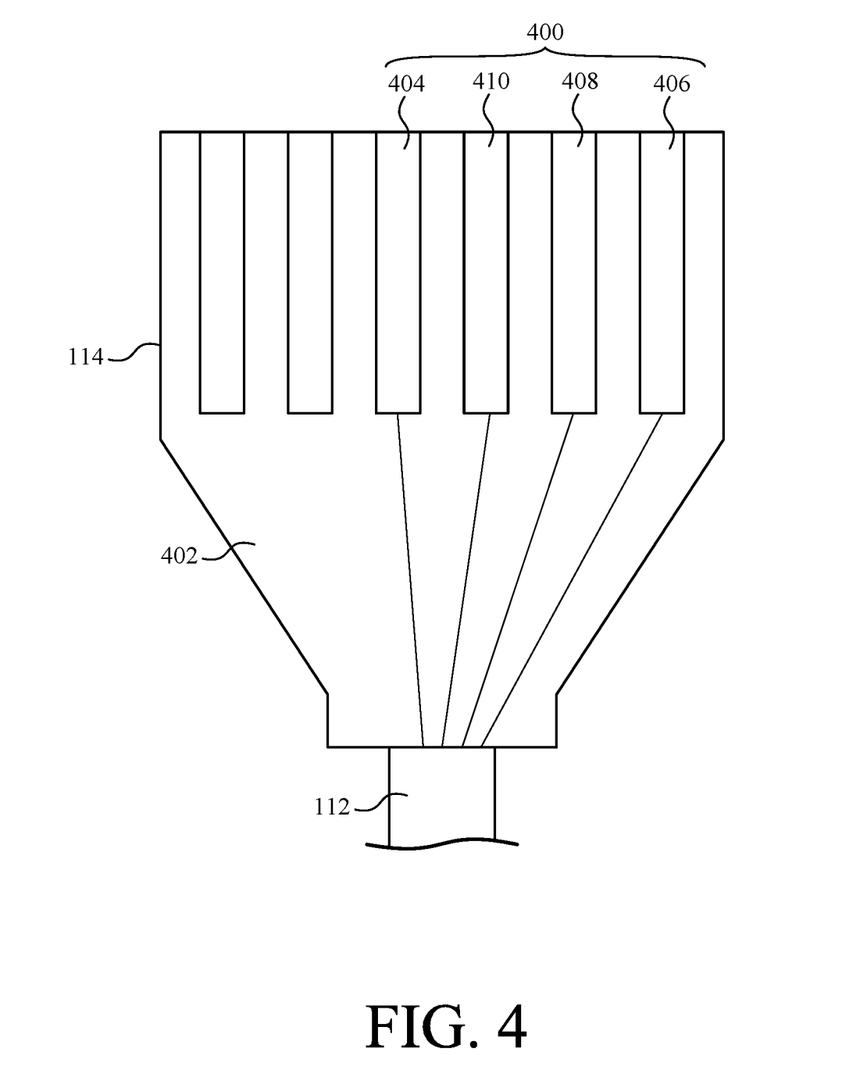
FIG. 4 shows a top view of the connector of FIG. 1.

FIG. 4 shows a front view of connector 114 attached to cable 112. Connector 114 is configured to electrically and physically connect endoscope 100 to system 102. Of course, endoscope 100 can also be disconnected from system 102 by removing connector 114 from socket 104 of system 102.

Connector 114 includes a set of electrical contacts 400 formed on a printed circuit board (PCB) 402. Contacts 400 are configured to engage a complimentary set of electrical contacts (not shown) of a host system such as, for example, system 102. Contacts 400 include a clock contact 404, an analog image signal contact 406, a power contact 408, and a reference contact 410. Clock contact 404 is electrically coupled to clock signal input terminal 300 of camera module 110 through cable 112, so that clock signals applied to clock contact 404 are provided to clock signal input terminal 300 of camera module 110. Analog image signal contact 406 is electrically coupled to analog image signal output terminal 302 of camera module 110 by cable 112, so the analog image signals output from terminal 302 of camera module 110 can be communicated to system 100 via analog image signal contact 406 of connector 114. Power contact 408 is electrically coupled to power terminal 304 of camera module 110 by cable 112, so that an operational voltage can supplied from system 102 to camera module 110 via power contact 408 of connector 114. Reference contact 410 is electrically connected to reference terminal 306 of camera module 110 by cable 112 and is configured to engage a reference (e.g. ground) terminal of system 102.

Figure 5:
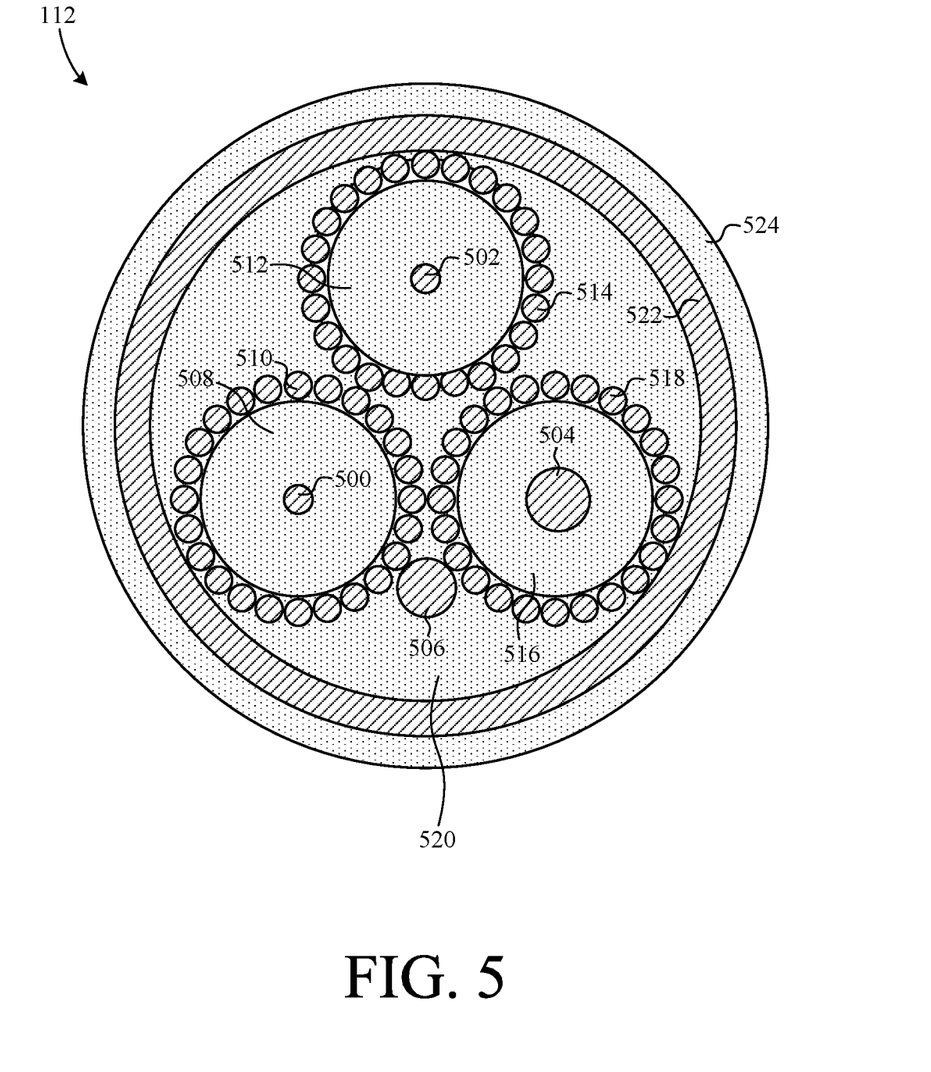
FIG. 5 is a cross-sectional view of the cable of FIG. 1 taken along line A-A of FIG. 1.

FIG. 5 shows a cross-sectional view of cable 112 taken along line A-A of FIG. 1. As previously mentioned, cable 112 includes a plurality of electrical wires that are electrically isolated from one another and have respective impedances that are specifically tailored to minimize noise that could otherwise degrade the quality of the signals transferred along cable 112.

Cable 112 includes a clock signal line 500, an analog image signal line 502, a power line 504, and a reference line 506. Clock signal line 500 is a wire having a first end electrically coupled to clock signal input terminal 300 of camera module 110, and an opposite second end electrically coupled to clock contact 404 of connector 114. Analog image signal line 502 is a wire having a first end electrically coupled to analog image signal output terminal 302 of camera module 110, and an opposite second end electrically coupled to analog image signal contact 406 of connector 114. Power line 504 is a wire having a first end electrically coupled to power terminal 304 of camera module 110, and an opposite second end electrically coupled to power contact 408 of connector 114. Reference line 506 is a wire having a first end electrically coupled to reference terminal 306 of camera module 110, and an opposite second end electrically coupled to reference contact 410 of connector 114.

Cable 112 further includes a plurality of insulators and conductive shields. Specifically, clock signal line 500 is coaxially disposed in an electrically insulating jacket 508, both of which are coaxially disposed in a conductive shield 510. Likewise, analog image signal line 502 is coaxially disposed in an electrically insulating jacket 512, both of which are coaxially disposed in a conductive shield 514. Power line 504 is coaxially disposed in an electrically insulating jacket 516, both of which are coaxially disposed in a conductive shield 518. Reference line 506 and conductive shields 510, 514, and 518 are also disposed in an electrically insulating material 520. Furthermore, an outer conductive shield 522 is disposed around clock signal line 500, analog image signal line 502, power line 504, reference line 506, insulating jacket 508, conductive shield 510, insulating jacket 512, conductive shield 514, insulating jacket 516, conductive shield 518, and insulation 520. Outer conductive shield 522 and all of the aforementioned components disposed therein are further disposed in an outer insulating jacket 524. Conductive shields 510, 514, and 518 are all in contact with each other and with reference line 506, thereby maintaining conductive shields 510, 514, and 518 at the reference voltage (e.g., ground).

In a particular example cable, the physical characteristics of the components are as follows.

Clock signal line 500, insulating jacket 598, and conductive shield 510 are arranged in a coaxial configuration. Clock signal line 500 is #42 AWG (American Wire Gauge) silver-copper alloy wire. Insulating jacket 508 is made of a perfluoroalkoxy (PFA) material and has an outer diameter of 0.2 mm±0.03 mm. Conductive shield 510 is a spiral 0.03 mm tinned copper alloy shielding wire.

Analog image signal line 502, insulating jacket 512, and conductive shield 514 are also arranged in a similar coaxial configuration. Analog image signal line 502 is #40 AWG silver-copper alloy wire. Insulating jacket 512 is PFA and has an outer diameter of 0.2 mm±0.03 mm. Conductive shield 514 is a spiral 0.03 mm tinned copper alloy shielding wire.

Power line 504, insulating jacket 516, and conductive shield 518 are also arranged in a coaxial configuration. Power line 504 is #40 AWG silver-copper alloy wire. The larger size of power line 504 limits the voltage drop along the length of the wire. Insulating jacket 516 is PFA and has an outer diameter of 0.2 mm±0.03 mm. Conductive shield 514 is a spiral 0.03 mm tinned copper alloy shielding wire.

Reference line 506 is a #40 AWG silver copper-alloy wire. Outer conductive shield 522 is a braided 0.05 mm tinned copper wire (coverage 90% min.) or, optionally, electromagnetic interference (EMI) tape. Outer insulating jacket is a PFA or polyester jacket with an outer diameter of 0.63 mm±0.1 mm.

Figure 6:
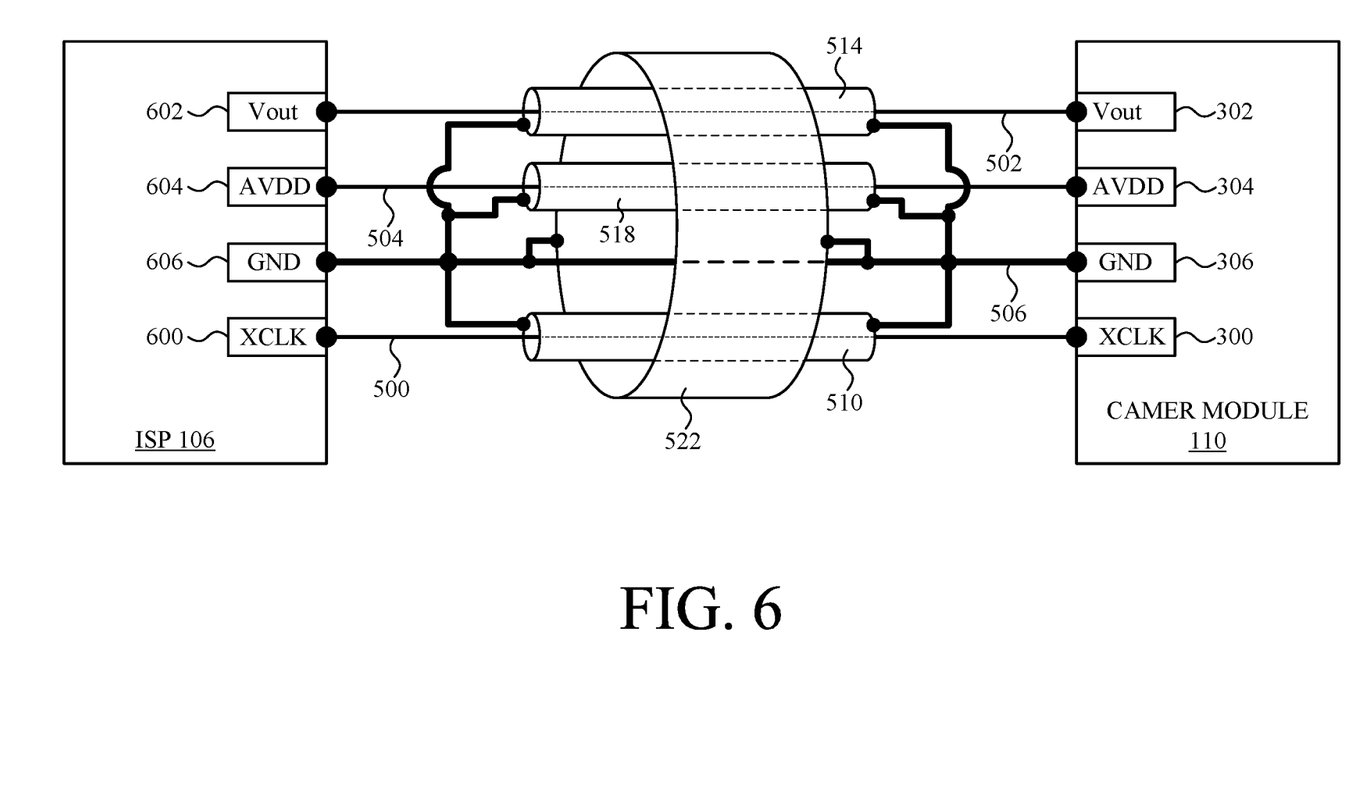
FIG. 6 is circuit diagram of the endoscope of FIG. 1 connected to the image signal processor of the host display system of FIG. 1.

FIG. 6 is a circuit diagram illustrating the electrical connection between camera module 110, cable 112, and ISP 106 when endoscope 100 is plugged into system 102. As shown, ISP 106 includes a clock signal output terminal 600, an analog image signal input terminal 602, a power terminal 604, and a reference terminal 606.

Clock signal output terminal 600 outputs clock signals (e.g. 4 MHz clock signal) to clock signal input terminal 300 of camera module 110 through clock signal line 500 of cable 112. Clock signal output terminal 600 of ISP 106, clock signal input terminal 300 of camera module 110, and clock signal line 500 of cable 112 are, therefore, all electrically connected to a common electrical node when endoscope 100 is plugged into system 102. The total electrical resistance for the XCLK connection between ISP 106 and camera module 110 is less than 150 ohms.

Analog image signal input terminal 602 receives analog image signals output from analog image signal output terminal 302 of camera module 110 through analog image signal line 502 of cable 112. Analog image signal input terminal 602 of ISP 106, analog image signal output terminal 302 of camera module 110, and analog image signal line 502 of cable 112 are, therefore, all electrically connected to a common electrical node when endoscope 100 is plugged into system 102. The total electrical resistance for the analog image signal connection (Vout) between ISP 106 and camera module 110 is less than 24 ohms. The total capacitance of the Vout connection is less than 0.82 nF and, to accommodate certain camera modules, can be less than 0.35 nF. The impedance of the connection is about 50 ohms.

Power terminal 604 provides power voltage to power terminal 304 of camera module 110 through power line 504 of cable 112. Power terminal 604 of ISP 106, power terminal 304 of camera module 110, and power line 504 of cable 112 are, therefore, all electrically connected to a common electrical node when endoscope 100 is plugged into system 102. The total electrical resistance for the power connection (AVDD) between ISP 106 and camera module 110 is less than 27 ohms.

Reference terminal 606 provides a ground to reference terminal 306 of camera module 110 through reference line 506 of cable 112. Furthermore, reference terminal 606 of ISP 106, reference terminal 306 of camera module 110, reference line 506 of cable 112, and shields 510, 514, 518, and 522 are all electrically connected to a common electrical node. The total electrical resistance for the reference connection (GND) between ISP 106 and camera module 110 is less than 2.0 ohms.

Figure 7:
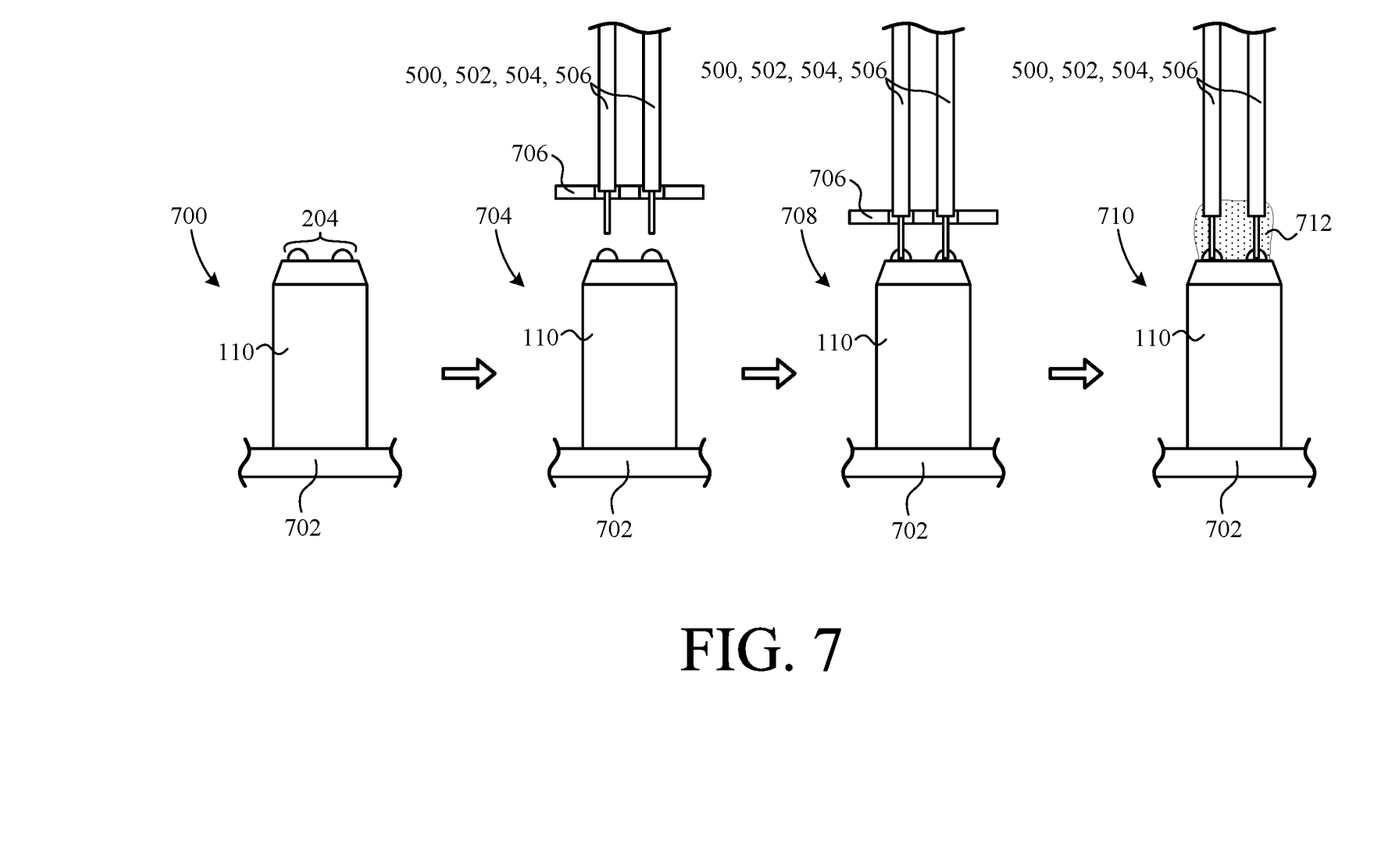
FIG. 7 depicts a method for electrically connecting the camera module of FIG. 1 to the wires of the cable of FIG. 1 according to an example embodiment.

FIG. 7 illustrates the steps of a method for electrically connecting camera module 110 to the wires of cable 112 during the manufacturing of endoscope 112. In a first step 700, the optical aperture end of camera module 110 is attached to a tape 702, with contacts 204 facing upward. Then, in a second step 704, an alignment tool 706 positions lines 500, 502, 504, and 506 over contacts 204 of camera module 110. Next, in a third step 708, lines 500, 502, 504, and 506 are soldered to respective terminals 300, 302, 304, and 306 by some suitable means such as, for example, laser soldering, hot-bar soldering, etc. Finally, in a fourth step 710, the solder joints are encapsulated by, for example, an epoxy 712 or other suitable material. The encapsulation of the solder joints provides structural reinforcement to the joints, provides a liquid-tight seal that prevents leakage into the joints, and prevents any short circuiting.

Figure 8:
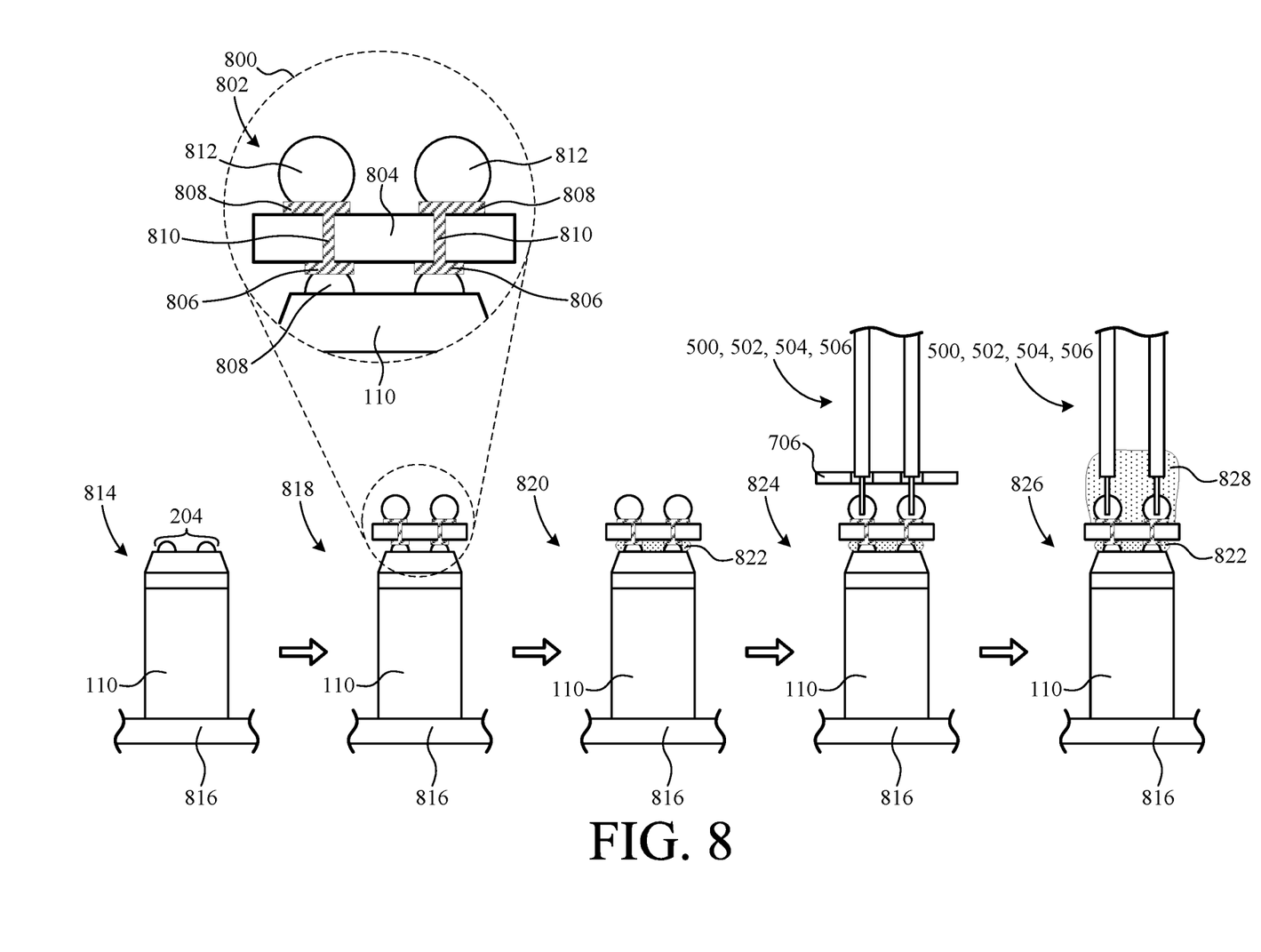
FIG. 8 depicts another method for electrically coupling the camera module of FIG. 1 to the wires of the cable of FIG. 1 according to another example embodiment.

FIG. 8 illustrates the steps of an alternate method for electrically connecting camera module 110 to the wires 500, 502, 504, 506 of cable 112 during the manufacturing of endoscope 112. As shown in the enlarged window 800, an intermediate plate assembly 802 is used to electrically connect camera module 110 to cable 112. Assembly 802 includes an electrically insulated plate 804 having a first side and a second side. The first side includes four contacts 806 (only two of the four are visible) configured thereon to be electrically connected to camera module 110. The opposite second side includes four (only two of the four visible) of contacts 808 configured thereon to be electrically connected to cable 112. In particular, each of contacts 806 is configured to be electrically connected to a respective one of clock signal input terminal 300, analog image signal output terminal 302, power terminal 304, and reference terminal 306 of camera module 110. Likewise, each of contacts 808 is configured to be electrically connected to a respective one of lines 500, 502, 504, and 506. Furthermore, each of contacts 806 is electrically connected to a respective one of contacts 808 through a respective conductive path 810 (e.g. electrical via) formed through plate 804. Each of contacts 808 includes a respective solder ball 812 formed thereon to facilitate the connection between assembly 802 and cable 112.

In a first step 814 of the method, the optical aperture end of camera module 110 is attached to a tape 816 with contacts 204 facing upward. Then, in a second step 818, assembly 802 is electrically coupled to camera module 110. That is, each of contacts 806 is electrically connected to a respective one of contacts 204. Next, in a third step 820, the electrical connection between assembly 802 and camera module 110 is encapsulated by, for example, a non-conductive epoxy 822 or the like. The encapsulation of the electrical connection between assembly 802 and camera module 110 with epoxy 822 provides structural reinforcement to the joints, provides a liquid-tight seal that prevents leakage into the joints, and prevents any short circuiting. Then, in a fourth step 824, alignment tool 706 positions each of lines 500, 502, 504, and 506 over a respective one of solder balls 812 and solder balls are heated (e.g., laser, hot-bar, etc.) to form respective electrical joints therebetween. Finally, in a fifth step 826, the solder joints between contacts 808 and lines 500, 502, 504, and 506 are encapsulated by additional non-conductive epoxy 828 or the like. The encapsulation of these solder joints provides structural reinforcement to the joints, provides a liquid-tight seal that prevents leakage into the joints, and prevents any short circuiting.

Figure 9:
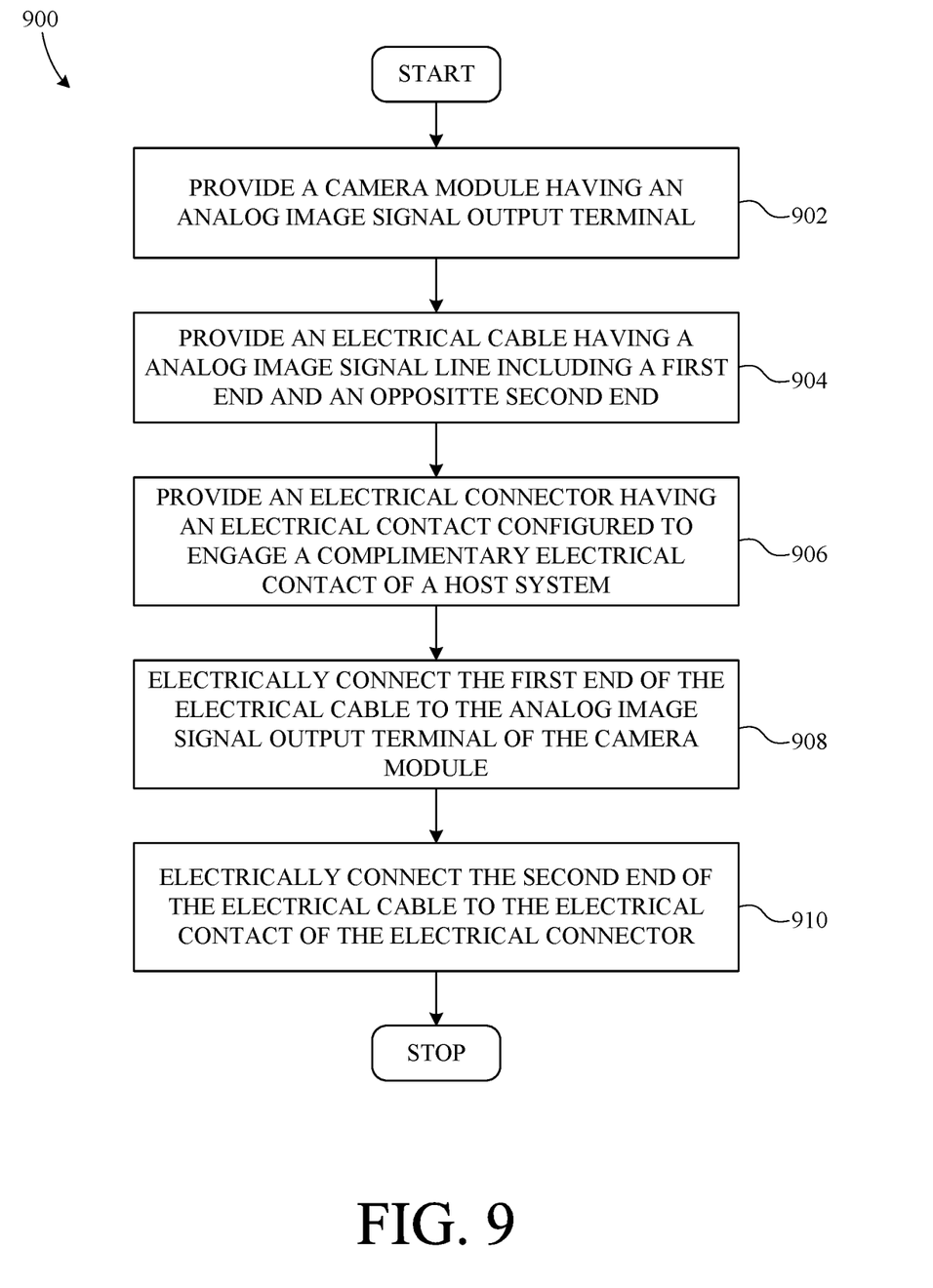
FIG. 9 is a flowchart summarizing a method of manufacturing an endoscope.

FIG. 9 is a flowchart summarizing a method 900 of manufacturing an endoscope. In a first step 902, a camera module having an analog image signal output terminal is provided. Then, in a second step 904, an electrical cable having an analog image signal line with a first end and a second end is provided. Next, in a third step 906, an electrical connector having an electrical contact configured to engage a complementary electrical contact of a host system is provided. Then, in a fourth step 908, the first end of the analog signal line of the electrical cable is electrically connected to the analog image signal output terminal of the camera module. Finally, in a fifth step 910, the second end of the electrical cable is electrically connected to the electrical contact of the electrical connector.

The description of particular embodiments of the present invention is now complete. Many of the described features may be substituted, altered or omitted without departing from the scope of the invention. For example, alternate electrical connections (e.g., stud bumps, wire bonds, etc.), may be substituted for the solder balls shown in the example embodiments. As another example, the electrical lines and shielding of the electrical cable may have different impedances tailored to function with particular alternate camera modules. As yet another example, alternate camera modules having an analog image signal output terminal may be substituted for the aforementioned camera modules of the example embodiments. As yet another example, the cable can include additional electrical lines to provide other functions/communications. However, limiting the number of electrical lines to 4 is considered to provide significant size and cost advantages. These and other deviations from the particular embodiments shown will be apparent to those skilled in the art, particularly in view of the foregoing disclosure.

We claim:

1. An endoscope comprising:
   a camera module including a clock signal input terminal, an analog image signal output terminal, a power terminal, and a reference terminal;
   a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module;
   an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line; and wherein
   said flexible electrical cable further includes a first electrically insulating jacket coaxially disposed around said analog image signal line;
   said flexible electrical cable further includes a first conductive shield coaxially disposed around said first electrically insulating jacket;
   said first conductive shield is electrically insulated from said analog image signal line; and
   said first conductive shield is in electrical contact with said reference line.

2. The endoscope of claim 1, wherein:
said flexible electrical cable further includes a second electrically insulating jacket coaxially disposed around said clock signal line;
said flexible electrical cable further includes a second conductive shield coaxially disposed around said second electrically insulating jacket;
said second conductive shield is electrically insulated from said clock signal line; and
said second conductive shield is in electrical contact with said first conductive shield and said reference line.

3. The endoscope of claim 2, wherein:
said flexible electrical cable further includes a third conductive shield disposed around and in electrical contact with said first conductive shield, said second conductive shield, and said reference line; and
a non-conductive sheath coaxially disposed around said third conductive shield.

4. The endoscope of claim 3, wherein:
said flexible electrical cable further includes a third electrically insulating jacket coaxially disposed around said power line;
said flexible electrical cable further includes a fourth conductive shield coaxially disposed around said third electrically insulating jacket;
said fourth conductive shield is electrically insulated from said power line;
said fourth conductive shield is in electrical contact with said first conductive shield, said second conductive shield, said third conductive shield, and said reference line; and
said third conductive shield is disposed around said fourth conductive shield.

5. The endoscope of claim 1, wherein said analog image signal line, said first electrically insulating jacket, and said first conductive shield are integral parts of a coaxial cable.

6. The endoscope of claim 1, further comprising an intermediate mount including:
a first side having
a first contact electrically connected to said first end of said clock signal line,
a second contact electrically connected to said first end of said analog image signal line,
a third contact electrically connected to said first end of said power signal line, and
a fourth contact electrically connected to said first end of said reference line;
a second side opposite said first side, said second side having
a first contact electrically connected to said clock signal input terminal of said camera module,
a second contact electrically connected to said analog image signal output terminal of said camera module,
a third contact electrically connected to said power terminal of said camera module, and
a fourth contact electrically connected to said reference terminal of said camera module; and wherein
said first contact of said first side of said intermediate mount is electrically coupled to said first contact of said second side of said intermediate mount;
said second contact of said first side of said intermediate mount is electrically coupled said second contact of said second side of said intermediate mount;
said third contact of said first side of said intermediate mount is electrically coupled to said third contact of said second side of said intermediate mount; and
said fourth contact of said first side of said intermediate mount is electrically coupled to said fourth contact of said second side of said intermediate mount.

7. The endoscope of claim 1, wherein the diameter of said power line is greater than the diameter of said analog image signal line.

8. The endoscope of claim 1, wherein the diameter of said power line is greater than the diameter of said clock signal line.

9. The endoscope of claim 1, further comprising
a conductive shield disposed around said clock signal line, said analog image signal line, said power line, and said reference line, and
a non-conductive sheath disposed around said conductive shield.

10. An endoscope comprising:
a camera module including a clock signal input terminal, an analog image signal output terminal, a power terminal, and a reference terminal;
a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module; and
an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line; and
a display system, said display system including
a complementary electrical connector configured to engage said electrical connector of said endoscope,
an image signal processor connected to receive an analog image signal via said complementary connector, and operative to process said analog image signal to produce digital image output, and
a display coupled to receive said digital image output from said image signal processor and operative to display images corresponding to said digital image output.

11. The endoscope of claim 10, wherein said reference line is a ground line.

12. The endoscope of claim 10, wherein:
said electrical connector includes a printed circuit board; and
said clock contact, said analog image signal contact, said power contact, and said reference contact are formed on said printed circuit board.

13. The endoscope of claim 10, wherein said connector is adhered to said cable.

14. The endoscope of claim 10, wherein said camera module is sealed to said cable.

15. The endoscope of claim 10, wherein:
said first end of said clock signal line is electrically connected directly to said clock signal input terminal of said camera module;

said first end of said analog image signal line is electrically connected directly to said analog image signal output terminal of said camera module;
said first end of said power line is electrically connected directly to said power terminal of said camera module; and
said first end of said reference line is electrically connected directly to said reference terminal of said camera module.

16. An endoscope comprising:
a camera module including a clock signal input terminal, an analog image signal output terminal, a power terminal, and a reference terminal;
a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module;
an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line; and
an intermediate mount including
    a first side having
        a first contact electrically connected to said first end of said clock signal line,
        a second contact electrically connected to said first end of said analog image signal line,
        a third contact electrically connected to said first end of said power signal line, and
        a fourth contact electrically connected to said first end of said reference line, and
    a second side opposite said first side, said second side having
        a first contact electrically connected to said clock signal input terminal of said camera module,
        a second contact electrically connected to said analog image signal output terminal of said camera module,
        a third contact electrically connected to said power terminal of said camera module, and
        a fourth contact electrically connected to said reference terminal of said camera module; and wherein
said first contact of said first side of said intermediate mount is electrically coupled to said first contact of said second side of said intermediate mount;
said second contact of said first side of said intermediate mount is electrically coupled to said second contact of said second side of said intermediate mount;
said third contact of said first side of said intermediate mount is electrically coupled to said third contact of said second side of said intermediate mount; and
said fourth contact of said first side of said intermediate mount is electrically coupled to said fourth contact of said second side of said intermediate mount.

17. The endoscope of claim 16, wherein:
said electrical connector includes a printed circuit board; and
said clock contact, said analog image signal contact, said power contact, and said reference contact are formed on said printed circuit board.

18. The endoscope of claim 16, wherein:
said first end of said clock signal line is electrically connected directly to said clock signal input terminal of said camera module;
said first end of said analog image signal line is electrically connected directly to said analog image signal output terminal of said camera module;
said first end of said power line is electrically connected directly to said power terminal of said camera module; and
said first end of said reference line is electrically connected directly to said reference terminal of said camera module.

19. The endoscope of claim 16, wherein the diameter of said power line is greater than the diameter of said analog image signal line.

20. The endoscope of claim 16, wherein the diameter of said power line is greater than the diameter of said clock signal line.

21. The endoscope of claim 16, further comprising
a conductive shield disposed around said clock signal line, said analog image signal line, said power line, and said reference line, and
a non-conductive sheath disposed around said conductive shield.

22. An endoscope comprising:
a camera module including a clock signal input terminal, an analog image signal output terminal, a power terminal, and a reference terminal;
a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module; and
an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line; and wherein
the diameter of said power line is greater than the diameter of said analog image signal line.

23. The endoscope of claim 22, wherein:
said first end of said clock signal line is electrically connected directly to said clock signal input terminal of said camera module;
said first end of said analog image signal line is electrically connected directly to said analog image signal output terminal of said camera module;
said first end of said power line is electrically connected directly to said power terminal of said camera module; and said first end of said reference line is electrically connected directly to said reference terminal of said camera module.

24. The endoscope of claim 22, wherein the diameter of said power line is greater than the diameter of said clock signal line.

25. The endoscope of claim 22, further comprising
a conductive shield disposed around said clock signal line, said analog image signal line, said power line, and said reference line, and
a non-conductive sheath disposed around said conductive shield.

26. An endoscope comprising:
a camera module including a clock signal input terminal, an analog image signal output terminal, a power terminal, and a reference terminal;
a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module; and
an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line; and wherein
the diameter of said power line is greater than the diameter of said clock signal line.

27. The endoscope of claim 26, wherein:
said flexible electrical cable further includes an electrically insulating jacket coaxially disposed around said clock signal line;
said flexible electrical cable further includes a conductive shield coaxially disposed around said electrically insulating jacket;
said conductive shield is electrically insulated from said clock signal line; and
said conductive shield is in electrical contact with said reference line.

28. An endoscope comprising:
a camera module including a clock signal input terminal, an analog image signal output terminal, a power terminal, and a reference terminal;
a flexible, electrical cable including a clock signal line having a first end coupled to said clock signal input terminal of said camera module, an analog image signal line having a first end electrically coupled to said analog image signal output terminal of said camera module, a power line having a first end electrically coupled to said power terminal of said camera module, and a reference line having a first end electrically coupled to said reference terminal of said camera module; and
an electrical connector including a set of electrical contacts configured to engage a complimentary set of electrical contacts of a host system, said set of electrical contacts including a clock contact electrically couple to a second end of said clock signal line, an analog image signal contact electrically coupled to a second end of said analog image signal line, a power contact electrically coupled to a second end of said power line, and a reference contact electrically coupled to a second end of said reference line;
a conductive shield disposed around said clock signal line, said analog image signal line, said power line, and said reference line; and
a non-conductive sheath disposed around said conductive shield.

29. The endoscope of claim 28, wherein:
said first end of said clock signal line is electrically connected directly to said clock signal input terminal of said camera module;
said first end of said analog image signal line is electrically connected directly to said analog image signal output terminal of said camera module;
said first end of said power line is electrically connected directly to said power terminal of said camera module; and
said first end of said reference line is electrically connected directly to said reference terminal of said camera module.

30. The endoscope of claim 28, wherein the diameter of said power line is greater than the diameter of said clock signal line.

* * * * *